United States Patent [19]

Ochi et al.

[11] Patent Number: 4,489,167
[45] Date of Patent: Dec. 18, 1984

[54] METHODS AND COMPOSITIONS FOR CANCER DETECTION

[75] Inventors: Yukio Ochi, Kyoto; Takashi Hachiya, Osaka; Tadayoshi Miyazaki; Yoshihiro Kajita, both of Kyoto, all of Japan

[73] Assignee: Baxter Travenol Laboratories, Inc., Deerfield, Ill.

[21] Appl. No.: 269,217

[22] Filed: Jun. 2, 1981

[51] Int. Cl.³ ............... G01N 33/54; G01N 33/56; G01N 33/58; A61K 43/00

[52] U.S. Cl. ................ 436/518; 260/112 R; 260/112 B; 424/1.1; 424/85; 436/531; 436/543; 436/544; 436/545; 436/546; 436/547; 436/800; 436/804; 436/813

[58] Field of Search ................ 424/1.1, 85; 436/542–547, 531, 800, 804, 813, 826; 260/112

[56] References Cited

U.S. PATENT DOCUMENTS

| | | | |
|---|---|---|---|
| 3,960,827 | 6/1976 | Bjorklund | 424/177 |
| 4,075,194 | 2/1978 | Sela et al. | 424/88 |
| 4,132,769 | 1/1979 | Osther | 424/9 |
| 4,140,753 | 2/1979 | Edgington et al. | 424/1 |
| 4,178,285 | 12/1979 | Felts et al. | 424/177 |
| 4,180,499 | 12/1979 | Hansen | 260/112 R |
| 4,198,389 | 4/1980 | Wadsworth | 424/3 |

OTHER PUBLICATIONS

Barbotte et al., Chemical Abstracts, vol. 86, 1977, Abstract #87384a.

Miyazaki et al., Clinica Chimica Acta, 122, (1982), 161–168.

*Primary Examiner*—Christine M. Nucker
*Attorney, Agent, or Firm*—Max D. Hensley; Paul C. Flattery; Marjorie D. Hunter

[57] ABSTRACT

Carcinoembryonic antigen contains immune determinates in common with α-acid glycoprotein. Carcinoembryonic antigen-containing compositions are purified by adsorption onto antibody to α-acid glycoprotein. The purified compositions may be employed as standards in carcinoembryonic antigen assays or in the labelled form as tracers. Intact carcinoembryonic antigen is assayed by a modified sandwich-type immunoassay. Other cancer-associated substances may be identified by searching for high molecular weight analogues of normal proteins.

24 Claims, No Drawings

4,489,167

METHODS AND COMPOSITIONS FOR CANCER DETECTION

FIELD OF THE INVENTION

This invention relates to methods and compositions for the diagnosis of cancer, in particular with methods for identifying cancer-associated proteins and for improving methods and compositions used in existing assays for carcinoembryonic antigen (hereinafter CEA).

BACKGROUND OF THE INVENTION

CEA is a heat stable glycoprotein having an isoelectric point at pH 4.5, a carbohydrate content of about 40–75% by weight, a high N-acetylglucosamine content (10–30% by weight), a trace of N-acetylgalactosamine and about from 4–20% by weight sialic acid. It is prepared by known methods from tumors or tissue culture. CEA is significant because elevated serum CEA concentrations have been associated with certain cancers, particularly those of the gastrointestinal tract. CEA tracers (labelled CEA analogues), CEA antibody and labelled CEA antibody are all known (U.S. Pat. Nos. 3,663,684 and 3,927,193).

$\alpha_1$ acid glycoprotein or orosomucoid (hereinafter AG) is heat stable and contains about 40–45% by weight carbohydrate, about 10% by weight sialic acid and aspartic acid, glutamic acid, methionine, N-acetylglucosamine and N-acetylgalactosamine in similar concentration to that in CEA. AG differs substantially from CEA in having an isoelectric point at pH 2.7, α-globulin electrophoretic mobility rather than β-globulin mobility and a molecular weight of about 45,000 rather than the approximately 200,000 of CEA. Insolubilized AG is known in the prior art. While various substances present in normal tissue are known which immunologically cross-react with CEA (nonspecific cross-reacting antigens or NCA), these substances have not been identified as having AG immune determinants.

It is an object of this invention to improve the sensitivity of known CEA assays and to provide a novel reagent for this purpose.

Another object of this invention is to provide a novel method and reagent for determining CEA.

A further object is to develop a novel method for screening the body fluids of cancer patients for cancer-associated substances that have diagnostic significance for cancer.

These and other objects will be apparent from consideration of the specification as a whole.

SUMMARY OF THE INVENTION

It surprisingly and unexpectedly has been found that there is a portion of the CEA molecule that has a marked immunochemical similarity to AG. This discovery has led to the following novel methods and compositions.

1. The sensitivity of CEA assays is improved by removing the proportion of CEA tracer and standards which does not cross-react with AG antibody. The removal is accomplished by binding the cross-reacting CEA to AG antibody as a receptor and recovering the CEA. This CEA exhibits higher affinity for CEA antibody than unadsorbed CEA compositions.

2. CEA assays are further improved by a novel method which measures only that CEA which exhibits both P segment and AG determinants. Labelled AG antibody is novel and is to be used in this method as described further below.

3. Unrecognized cancer-associated substances may be identified by analogy to the relationship discovered between AG and CEA. Normal proteins or acute phase reactants are selected and their larger molecular weight analogues or conjugates are sought in the body fluids of cancer patients. If such large molecules are found in normal body fluids in a different concentration than in the body fluid of cancer patients, or are not found in normal body fluids at all, then it is concluded that the large molecule is cancer-associated.

DETAILED DESCRIPTION OF THE INVENTION

The CEA preparations to be purified in accordance with the method herein may be obtained by any conventional method. CEA is ordinarily obtained by extraction of tissue cultures or tumors, e.g. hepatic metastases of gastro-intestinal cancers. A suitable method for making a CEA-containing starting material is disclosed in U.S. Pat. No. 3,663,684. Other less complex methods may be satisfactory, however. For example, the cell or tissue sample may be homogenized in water, extracted with a glycoprotein solvent such as perchloric acid (or heated at 70° C. to precipitate heat denaturable proteins), centrifuged to remove insoluble matter, residual perchloric acid removed by dialysis or potassium perchlorate precipitation (U.S. Pat. No. 4,180,556) and the CEA recovered. The CEA may be labelled in known manner with a suitable detectable group such as a radioisotope, enzyme, stable free radical, coenzyme, fluorescent group, chemiluninescent group or enzyme inhibitor or activator, either before or after the purification procedure which is described below.

The objective of the purification method herein is to prepare native or labelled CEA compositions which are enriched in, or consist essentially of CEA which is cross-reactive with AG antibody. A substantial portion of commercially available radioiodinated CEA will not bind or binds very weakly to AG antibody. For example, only about one third of the radioactivity in such radioiodinated CEA preparations will bind to AG antibody immediately, while less than about 50% of the radioactivity will bind even after an overnight incubation. The identity of the unbound portion of the CEA preparations is unknown at present. It may contain contaminating proteins.

While a proportion of CEA preparations will bind to AG antibody, it is interesting to note that CEA antibody will not bind AG. This paradox is believed to be a function of the method by which CEA antibody is made. CEA antibody is conventionally prepared by immunizing an animal with CEA preparations, thus leading to the generation of antibodies specific for both the AG determinant of CEA, other CEA determinants and contaminants in the CEA preparation. Then the antiserum is incubated with normal tissue with the intention of removing "non-CEA" antibodies raised against the contaminants in the immunizing CEA preparation. However, the antibody population raised against CEA also includes antibody specific for a normal tissue component, AG. Thus the AG antibody is removed by incubation with normal tissue. The remaining CEA antibody therefore is only directed at that portion of CEA which is not cross-reactive with AG antibody, i.e., which does not have immune sites similar to those of AG. This portion is designated hereinafter to be the P segment of CEA. Antibody specific for this segment is the CEA P-segment antibody. CEA which contains both the P segment and AG immune sites is hereinafter referred to for convenience as intact CEA.

The preferred method for purifying intact CEA entails adsorbing an impure starting composition with AG antibody, removing the unbound residue of the starting composition and separating the CEA from the AG antibody. It is not necessary to first separate CEA from any AG which may be present in the impure composition: The binding affinity of AG to AG antibody is significantly higher than that of intact CEA. Thus, careful selection and control of the conditions for eluting the AG antibody-bound CEA to leave the AG bound to its antibody will enable the separation of CEA from AG based on the differing affinity of the two substances for AG antibody.

A more elaborate procedure comprises contacting the impure CEA-containing composition with antibody capable of binding only the CEA P segment, separating the bound material from the composition residue, separating the adsorbed CEA from the antibody to form an intermediate composition, binding the intact CEA in the intermediate composition to AG antibody, separating the bound, intact CEA from the residue and separating the intact CEA from AG antibody.

The foregoing steps which involve separating an antibody having bound CEA from a residue of unbound material may be accomplished by any known method for separating antibodies from solution. Such methods usually entail insolubilizing the antibody. This may be done either before or after the binding of antibody to CEA.

Preferably the antibody is made water insoluble before it is contacted with CEA. This may be accomplished by covalently linking the antibody to a water insoluble carrier (Biou et al. "Clin. Biochem."[Ottawa]10[4]: 141-7 [1977]) or adsorbing the antibody noncovalently onto a suitable carrier (Wang et al. "Clin. Chem." 25 [4]: 546-9 [1979]). Representative carriers include polyols such as cross-linked dextrans, cellulose, glass or nylon. The carriers may be in the form of fibrous masses, beads or granules. When the carriers are linked to the antibody by covalent bonds, an organic linking group such as an amide, ether or ester is used to covalently bond the antibody to the carrier. Suitable techniques for insolubilizing the antibody are readily selected by the artisan and are not critical to this invention.

AG antibody and CEA P segment antibody are commercially available, or they may be prepared by known methods. AG antibody is readily produced in experimental animals such as rabbits or goats by immunizing with a solution of AG in an adjuvant.

CEA P segment antibody is manufactured by preparing CEA as described above and immunizing experimental animals, followed by adsorption of the antiserum on normal tissue from the same source as the CEA. This last step is generally conventional and has as its purpose the removal of antibodies to normal, non-CEA contaminants that may have been present in the CEA preparation used to immunize the animal, although as noted above it also removes AG antibody. The antisera from the immunized animal may be used as such or further purified in known fashion, e.g., by chromatography, electrophoresis and the like as desired.

Typically, intact CEA is recovered from labelled or native, i.e., unlabelled, CEA preparations by conjugating antibody to a cyanogen bromide activated, cross-linked dextran. The insoluble antibody is packed into a column and equilibrated with a buffer at near neutral pH. The labelled or native CEA is mixed with normal serum to aid in reducing nonspecific binding in the column. Then the CEA composition is applied to the column, ordinarily at room temperature. The time for the composition to remain in contact with the antibody will vary from several minutes (the passage time) to about 24 hours. About 10 hours is generally preferred. The time is not critical, although longer incubation periods will yield larger CEA recoveries.

After the incubation is complete the residual, unbound fraction is eluted from the column with buffer held near neutrality. Then the bound fraction is eluted with a release agent. Any substances or conditions known to disrupt antigen-antibody complexes may be used as release agents. Examples in addition to acids include urea and salts. The elution step is optimized to minimize AG elution while maximizing CEA elution. With this in mind the artisan will adjust the elution conditions and select suitable eluants depending upon the nature of the starting composition, the insoluble antibody, the degree of purification desired, whether the CEA is labelled or not and, if so, the nature of the label. Such optimization adjustments are well within the skill of the ordinary artisan.

The recovered intact labelled or native CEA may be purified further to remove residual AG if desired and lyophilized or stored frozen until use. The purified, intact CEA may be put to any use heretofore suitable for CEA, e.g., as a tracer (labelled analogue) in known CEA assays or as an immunogen for making CEA antibody. Use of purified CEA tracer as prepared above increases the sensitivity of immunoassays to the point that the perchloric acid or heat extraction of samples as practiced in known assays can be eliminated and untreated samples such as sera used directly.

IMMUNOASSAYS

It is within the scope of this invention to employ the purified labelled CEA prepared above in a typical competitive-type immunoassay This means that labelled CEA and test sample CEA compete for a limited number of CEA antibody binding sites, after which the antibody-bound material is assayed for label. If a large amount of sample CEA is present then most labelled CEA will be displaced competitively from the antibody, and the converse if the sample is low in CEA. Considerable improvement in commercial radioimmunoassays sold by Hoffmann La Roche and CIS can be obtained with labelled CEA which is substantially free of proteins which are not bound by antibody to AG, i.e., labelled CEA which contains less than about 40% proteins which are not so bound. The purified, labelled CEA is significantly more immuno reactive with the CEA antibody than is the unpurified tracer. The problem is that the CEA heretofore was perceived by the art to be largely homogeneous, when in fact the presence of AG and P segment determinants in intact CEA suggests than an unknown proportion of test sample CEA may exhibit only P segment determinants. It is hypothesized that the sample P segment will compete with labelled and test sample, intact CEA in conventional competitive type immunoassays, thereby interfering with the assay of intact CEA. This potential interference is eliminated by selecting an assay protocol that takes it into account. Accordingly, the improvement of this invention comprises determining only intact CEA, i.e., that which contains immunologically expressed determinants common to both AG and the P segment. This may be accomplished by stripping any non-AG antibody cross-reactive material from the test sample in a preliminary purification and the sample then assayed by a competitive system. However, the preferred embodiment is a modified "sandwich" technique. The "sandwich" immunoassay is well known. In general, the reagents used in this assay are an insoluble antibody to the analyte and a labelled soluble antibody to analyte. An amount of insoluble antibody is used which contains fewer analyte binding sites than the expected test sample analyte population. The assay is generally conducted by sequentially contacting the insoluble antibody with test sample and then labelled antibody, followed by assaying the bound label. The analyte is "sandwiched" between the insoluble and the labelled antibody. This requires of course that the analyte have at least two immune binding sites. The potential presence of CEA P segment in assays for intact CEA makes one modification of the assay desirable: The soluble labelled antibody is not the same antibody as the insoluble antibody, even though both antibodies bind the analyte, i.e., one antibody is directed against P segment determinant of intact CEA while the second antibody is capable of binding of CEA AG determinant. This prevents either of AG or the P segment from mimicking intact CEA.

The modified sandwich method comprises
(a) contacting the test sample with a test matrix comprising water insoluble antibody to the P segment of CEA;
(b) removing the test sample residue;
(c) contacting the test matrix with labelled antibody to AG;
(d) removing the unbound, labelled antibody; and
(e) determining the amount of bound or unbound label.

For purposes of illustration, the final product of the method will be

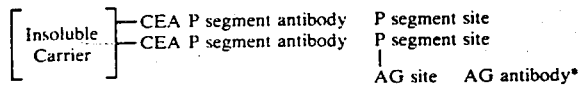

where is an immune bond and * is a label. The bound CEA P segment is not bound by labelled antibody and therefore is not assayed as CEA. Any P segment CEA which may be present does not bind the AG antibody.

The antibodies do not need to be directed against a single determinant of the P or AG segments of intact CEA. A variety of antibodies capable of binding two or more separate immune sites may be used. Of course, the P segment antibody or antibodies must not be cross-reactive with AG, and the AG antibody must not bind the CEA P segment. Nonetheless, each antibody is desirably as uniform as possible; i.e., one should use a single antibody directed against a single immune site, such as can be obtained by hybridoma culture in known fashion.

The P segment antibody may be insolubilized in the same way as AG antibody is prepared body. Preferably, antibody is insolubilized by adsorbing it to the surface of a polystyrene bead or the inner bottom surface of a polypropylene test tube.

Labelled antibody to AG is believed to be novel. Any of the labels described above for CEA may be employed with the AG antibody, which is prepared in the same fashion as other labelled antibodies. See for example U.S. Pat. No. 3,927,193, which discloses a method for making radiolabelled antibody to CEA. The preferred labels are enzymes and radioisotopes, most preferably radioiodine. Suitable methods for radioiodination use chloramine-T or lactoperoxidase, e.g., as disclosed by Dermody et al., "Clinical Chemistry" 25 (6):989–995 (1979) or Parsons et al., "Analytical Biochemistry" 95:568–574 (1979), externally radioiodinated small molecules such as ($^{125}$i) iodohydroxyphenyl propionate-N-hydroxysuccinimate ester (Bolton et al., "Biochem. Journal" 133:529–533 [1973]). ($^{125}$i) diiodofluorescein isothiocyanate (Gabel et al., "Analytical Biochemistry" 86:396–406 [1973]), tertiary-butoxycarbonyl-L-($^{125}$i) iodotyrosine-N-hydroxysuccinimide ester (Assoian et al., "Analytical Biochemistry" 103:70–76 [1980]), or IC1 (Montelaro et al., "Analytical Biochemistry" 99:92–96 [1979]). The chloramine-T method is the preferred embodiment.

The particular method which is selected for determining intact CEA is not critical. Other methods than those described above will be apparent to the skilled artisan.

SCREENING METHOD

The discovery that CEA contains antigenic determinants similar to AG suggests a method for identifying cancer markers other than CEA, markers which at the present time are completely unknown.

AG is normally found in the circulation, but its concentration is frequently elevated in the serum of cancer patients. Unfortunately, AG concentrations are also elevated in other instances of rapid cell proliferation, e.g., as a result of inflammation attendant pregancy and various unrelated disease states including pneumonia, arthritis and wound healing. Thus, unlike CEA the clinical significance of AG as a specific cancer marker has not been widely acknowledged because of the high level of false positives. The molecular weights of CEA and AG are about 200,000 and 45,000, respectively. Thus the normal protein AG, even though an acute phase reactant which is elevated in cancer, is not diagnostically significant while the "big" form of the protein, CEA, is considered diagnostically useful.

It is our hypothesis that this newly discovered relationship between a clinically significant, high molecular weight glycoprotein (CEA) and a lower molecular weight, acute phase protein present in unelevated amounts in normal serum (AG) indicates that in cancer the precursor forms of proteins found in normal serum are released into the extracellular environment. The amounts of such precursors can then be determined as an aid to cancer diagnosis and therapy monitoring. The underlying reason for the presence of extracellular precursors is not known, but may be hypothesized to be a function of the deranged metabolism of cancer cells. It has been demonstrated in many cases that intracellular precursors of peptide hormones or proteins are of larger molecular weight than the circulating, biologically active product peptide hormones or proteins.

As a corollary, the specific normal proteins which are the most likely candidates for having circulating high molecular weight precursors are the acute phase reactants such as AG. These are generally glycoproteins found in higher concentrations than normal in a variety of disease states including cancer.

Pursuant to this hypothesis a method is provided for identifying cancer-associated substances, comprising (a) selecting a protein present in a body fluid of a cancer-free donor, (b) obtaining a body fluid from a donor having a known cancer, (c) identifying in the body fluid of part (b) at least one molecule having at least one antigenic determinant in common with said selected protein but which is of larger molecular weight than said selected protein, and (d) comparing the amount of the molecule present in a body fluid of cancerous and cancer-free donors.

This method is readily practiced using known procedures. The simplest embodiment as presently conceived is an immune affinity chromatography technique. The first step is to isolate a candidate protein which is present in a body fluid such as blood, sera, lymph or urine. It is not necessary to know what the protein is, but it should be purified to the point that it is substantially homogeneous by electrophoresis and gel chromatography. This protein may or may not be present in the sera or body fluids of cancer patients. However, the protein should be selected from donors thought to be cancer-free so as to avoid the possibility that the selected protein might be a cancer-associated substance in its own right. By "protein", it is meant only that the isolated molecule has at least one antigenic determinant; it may be substituted or associated with lipids, carbohydrates or other non-peptidyl moieties. A fruitful area for screening would be the glycoproteins in general and known acute phase reactants in particular. It is not necessary that the protein be isolated de novo from the body fluid. It may be a known, fully characterized protein available in relatively purified form from commercial sources.

Once the selected protein has been isolated, antisera to the protein is raised in laboratory animals. This is done in conventional fashion, or the antibody may be obtained from commercial supplies if available. In either case it may be desirable to purify the antisera by affinity chromatography on insolubilized selected protein, e.g., covalently bonding the protein to cyanogen bromide-activated, cross-linked dextran, packing into a column, passing the antiserum through the column, and eluting the antibodies with pH 2.5 buffer. The antibodies may also be purified by immunoprecipitation in the presence of polyethylene glysol.

The next step will reveal whether any potential cancer-associated substances are present in the selected body fluid of cancer patients. Put simply, one attempts to identify molecules which share at least one antigenic determinant with the selected protein but which are of larger molecular weight than the selected protein. If such molecules follow the relationship found between CEA and AG they will be conjugates of at least a portion of the selected protein and at least one polypeptide. The first element of this step is the isolation of proteins which cross-react with the selected protein. This is readily accomplished by known procedures. Again, affinity chromatography with insolubilized antibody to selected protein (produced in the same way as the insolubilized CEA P segment or AG antibodies described elsewhere herein) or immune precipitation is satisfactory. The usual antigen elution agents such as acid, urea or salts should be selected to optimize elution of cross-reacting (or identical) proteins to the selected protein.

If the eluted protein is not homogeneous the discrete proteins should be separated by molecular weight so that each protein can be compared to the selected protein. This is most readily accomplished by sucrose or cesium chloride density gradient ultracentrifugation with the selected protein as a control. All molecules which exhibit a molecular weight the same or smaller than the selected protein are discarded and the higher molecular weight fraction or fractions are recovered as candidate cancer-associated molecules. The "same" molecular weight means as identical weight within the experimental error of the separation technique.

Another suitable separation method is to ultrafilter the molecules against a membrane having a molecular weight cut-off about ten percent higher than the molecular weight of the selected protein. Here, the retentate is recovered for further investigation. However, if the retentate contains more than one candidate protein the proteins should be separated. Here it is not necessary that the proteins be further separated by molecular weight. Instead, electrophoresis and ion exchange or gel chromatography may be employed in place of ultracentrifugation.

The final step in identifying cancer-associated proteins is to determine the amount of the candidate molecule which may be present in a body fluid of cancer-free donors. The molecule is cancer associated if the body fluid contains a different concentration or activity of the molecule compared to the amount in the same body fluid of cancer patients. Usually, it should be expected that the molecule will be absent in detectable amounts from the body fluid of cancer-free donors.

Methods for determining the amount of the molecule in noncancer body fluid are well within the skill of the art. Preferably, a qualitative or semi-quantitative method such as electrophoresis is used to initially determine whether or not any detectable quantity of the molecule is present in the noncancer body fluid. If the molecule is detected then more quantitative methods will be required to determine the amount or activity of the molecule. Such methods include solid phase immunoassays such as radioimmunoassays, enzyme-linked immunoadsorbent assays or nephelometry. An example of a typical immunoassay which could be used is the "sandwich" assay disclosed in Example 2, except that the assay would be designed in known fashion to determine the candidate molecule rather than CEA and neither antibodies need have any specificity for a particular segment of the test molecule, i.e., the same original antibody could be used for the immobilized and labelled reagents. Obviously, the assays for both the candidate molecule and the selected protein will be developed depending on the nature of the substances to be determined. For example, if the molecule contains a plurality of immune sites (as will generally be the case) then a sandwich immunoassay may be employed. On the other hand, if the selected protein is a low molecular weight polypeptide, e.g., on the order of 1,000 to 3,000 molecular weight, then a competitive radioimmunoassay is called for. The immobilized antibody and labelled antibody or protein reagents to be used in such assays may be made in the same fashion as described elsewhere herein.

The invention is further described in the following examples.

EXAMPLE 1

AG antibody (Hoeschst or Miles) was labelled with $^{125}i$ according to this contemplated example and the method of Greenwood et al., "Biochem. J" 89:114–123 (1963). 50 ug aliquots of antibody were treated by the Greenwood et al. method and separated from free iodine by passage through a column of Sephadex G-50. The labelled antibody fraction is diluted to about 3 uCi/ml in a diluent of 5% calf serum and an antibacterial agent, 0.1% $NaN_3$. The preparation is stored at 4° C.

EXAMPLE 2

This method describes a contemplated modified sandwich immunoassay to determine intact CEA.

CEA was purified from hepatitic metastasis of primary adenocarcinoma of the colon by homogenizing the tissue in an equal volume of distilled water in a Waring blender. The homogenate is clarified by centrifugation at 8,000 rpm for 30 min. at 5° C. The supernatant was mixed with 1M perchloric acid and the precipitate removed by centrifugation. The supernatant was dialyzed against distilled water for 5 days.

The perchloric acid-extracted fraction containing 50 mg protein/ml was purified by gel filtration on a Sephadex G-200 column (170×1.5 cm) equilibrated with 0.05M phosphate buffer at pH 7.8. The effluent was collected in 4 ml aliquots and monitored at 280 nm for protein and for CEA by radioimmunoassay. The first protein peak (void volume) of the effluent was collected and concentrated, then the gel filtration repeated.

CEA P segment antibody was made by emulsifying 5 mg of the CEA preparation above in complete Freund's adjuvant, injecting the emulsion into a rabbit, harvesting 20 ml of serum after the CEA titer had risen and adsorbing the antiserum to both non-cancerous liver tissue and normal human serum. The preparation was stored at 4° C.

About 1 ml of CEA P segment antiserum was coated on the bottom of the inner surface of a polypropylene test tube according to U.S. Pat. No. 3,686,346. 0.1 ml of serum sample from a patient known to have an adenocarcinoma of the bowel and 0.1 ml of a normal control were pipetted into replicate coated tubes and incubated for 12 hours. The unbound sample was washed from each tube with water, 0.3 ml of labelled AG antibody prepared in Example 1 added to each tube, the tubes incubated for 24 hours, unbound labelled antibody washed from the tubes with water and the radioactivity bound to the tube determined. The average radioactivity bound in the sample test tube was significantly greater than that in the control

EXAMPLE 3

This example describes the purification of a radioiodinated CEA preparation (Hoffmann La Roche, 22 1,000,000 cpm). Insoluble antibody to AG was made by conjugating 300 mg of AG antibody (gamma globulin-Dako) to 30 ml of cyanogen bromide-activated Sepharose 4B (Pharmacia). The insolubilized antibody was packed into a 5×1.0 cm column.

One aliquot of $^{125}i$ labelled CEA was mixed with normal rabbit serum, applied to the column and eluted with 0.05M phosphate buffer, pH 7.8, immediately after application while a second aliquot was applied to the column, incubated overnight at 5° C., 0.1 ml of normal rabbit serum applied to the column and the column eluted with the phosphate buffer. These fractions are designated the unbound fractions. The bound fractions were eluted in both cases with 0.1M glycine buffer at pH 2.2 after the unbound fractions had been collected. The eluted fractions in glycine buffer were adjusted to pH 7.8 by 1M tris buffer. The radioactivity of each fraction was counted. Table 1 records the results.

TABLE 1

| | Percent | | |
|---|---|---|---|
| Elution | Applied Radioactivity | Bound Radioactivity | Unbound Radioactivity |
| Immediate | 100 | 28 | 68 |
| Overnight | 100 | 40 | 54 |

Bound and unbound radioactivity did not total 100% because a small residue of tracer was retained by the column. Similar results were obtained by a polyethylene glycol-enhanced precipitation of the radioiodinated CEA with AG antibody from two other sources (Hoechst and Miles Laboratories). Almost all bound, eluted radioactivity was precipitated by either AG antibody (Dako) or CEA antibody, but no significant precipitated radioactivity compared to a control was found in the unbound fraction. The CEA binding to AG antibody was shown to be immunospecific because (1) AG displaced CEA radioactivity from AG antibody in a dose-dependent relationship with (2) antisera against other serum proteins did not precipitate the CEA.

The bound, eluted fraction was employed in place of the unpurified tracer in commercial kits for CEA determination (CiS and Hoffman La Roche).

We claim:

1. A method comprising
   (a) contacting an impure CEA (carcinoembryonic-antigen) or labelled CEA containing composition with an antibody to AG (acid-glycoprotein),
   (b) removing the unadsorbed residue of the composition
and
   (c) separating the CEA or labelled CEA from said antibody.

2. The method of claim 1 further comprising
   (a) contacting an impure, CEA or labelled CEA containing composition with antibody to CEA whereby the CEA or labelled CEA is adsorbed,
   (b) separating the CEA antibody and bound CEA or labelled CEA from the composition residue,
   (c) separating the CEA or labelled CEA from said antibody to yield an intermediate composition,
   (d) contacting the separated CEA or labelled CEA with antibody to AG whereby a proportion of the intermediate composition is adsorbed,
   (e) separating the adsorbed CEA or labelled CEA from the residue of the intermediate composition
and
   (f) separating the CEA or labelled CEA from the antibody to AG.

3. The method of claim 1 wherein the antibody is insolubilized and the CEA or labelled CEA is separated from AG antibody by eluting with acid.

4. The method of claim 1 wherein the antibody is insolubilized and the unabsorbed composition residue is removed by washing the antibody.

5. The method of claim 1 wherein the antibody is insolubilized.

6. The method of claim 5 wherein the antibody is insolubilized by covalent linkage to a water insoluble carrier.

7. The method of claim 6 wherein the covalent linkage is an organic linking group intermediate the antibody and the carrier.

8. The method of claim 7 wherein the linking group is an amide, an ester or an ether.

9. The method of claim 6 wherein the carrier is a water insoluble polyol.

10. The method of claim 5 wherein the antibody is insolubilized by non-covalent and adsorption onto a water-insoluble carrier.

11. The method of claim 10 wherein the carrier is a polyolefin.

12. The method of claim 11 wherein the carrier is granular.

13. The method of claims 1 or 2 wherein the CEA is unlabelled and the impure, CEA-containing composition is a tumor extract.

14. A method for assaying CEA in a test sample, comprising
 (a) contacting the test sample with a test matrix comprising water insoluble antibody to the P segment of CEA,
 (b) removing the test sample residue,
 (c) contacting the test matrix with labelled antibody to AG;
 (d) removing the unbound, labelled antibody; and
 (e) determining the amount of bound or unbound label.

15. The method of claim 14 wherein the test sample residue and the unbound, labelled antibody are removed from the test matrix by washing.

16. The method of claim 14 wherein the test matrix is a polyolefin test tube and the antibody is rendered water insoluble by adsorption to the inner surface of the test tube.

17. Water soluble antibody to AG labelled with a detectable moiety.

18. The antibody of claim 17 wherein the moiety is a radioisotope.

19. The antibody of claim 17 wherein the moiety is an enzyme.

20. The antibody of claim 17 wherein the moiety is a fluorescent group, a stable free radical, a coenzyme, a chemiluminescent group or an enzyme modulator.

21. A composition comprising CEA or labelled CEA which is substantially free of proteins which are not bound by antibody to AG.

22. A composition consisting essentially of intact CEA or intact, labelled CEA which composition is substantially free of the P segment of CEA.

23. The composition of claims 21 or 22 wherein the CEA is labelled with an enzyme or a radioisotope.

24. In a method for determining CEA in a test sample wherein labelled CEA and test sample CEA compete for a limited number of CEA antibody binding sites, after which the antibody-bound material is assayed for label and compared with CEA standards assayed by the same procedure, the improvement comprising the CEA or the labelled CEA separated in accord with claims 1 or 2.

* * * * *